(12) United States Patent
Patnala et al.

(10) Patent No.: US 11,433,246 B2
(45) Date of Patent: Sep. 6, 2022

(54) SLOTTED STIFFENING MEMBER FOR FACILITATING AN INSERTION OF AN ELECTRODE LEAD INTO A COCHLEA OF A PATIENT

(71) Applicant: Advanced Bionics AG, Staefa (CH)

(72) Inventors: Anil K. Patnala, Stevenson Ranch, CA (US); Kurt J. Koester, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 91 days.

(21) Appl. No.: 16/767,969

(22) PCT Filed: Nov. 30, 2017

(86) PCT No.: PCT/US2017/064035
§ 371 (c)(1),
(2) Date: May 28, 2020

(87) PCT Pub. No.: WO2019/108210
PCT Pub. Date: Jun. 6, 2019

(65) Prior Publication Data
US 2021/0001128 A1    Jan. 7, 2021

(51) Int. Cl.
*A61N 1/37* (2006.01)
*A61N 1/375* (2006.01)
(Continued)

(52) U.S. Cl.
CPC .......... *A61N 1/375* (2013.01); *A61N 1/0541* (2013.01); *A61N 1/36038* (2017.08)

(58) Field of Classification Search
CPC .............................. A61N 1/375; A61N 1/0541
See application file for complete search history.

(56) References Cited

U.S. PATENT DOCUMENTS 5,123,422 A * 6/1992 Charvin ............... A61N 1/0541
607/137
5,123,522 A * 6/1992 Comly, Jr. .............. B65B 61/28
198/779
(Continued)

FOREIGN PATENT DOCUMENTS

| CN | 107847735 | 7/2016 |
| CN | 106178260 | 12/2016 |

(Continued)

OTHER PUBLICATIONS

International Search Report and Written Opinion received in International Application No. PCT/US17/064035, dated Aug. 30, 2018.

(Continued)

*Primary Examiner* — Eric D. Bertram
(74) *Attorney, Agent, or Firm* — ALG Intellectual Property, LLC

(57) ABSTRACT

An exemplary stiffening member facilitates insertion of an electrode lead into a cochlea of a patient. The stiffening member includes an elongate body configured to integrate with the electrode lead so as to maintain the electrode lead in a substantially linear configuration in an absence of a flexure force on the body. The stiffening member further includes compression slots distributed along a first side of the body closer to the electrodes than a second side while the body is integrated with the electrode lead. The compression slots are configured to compress, in a presence of the flexure force, so as to bias the body to flex in an inward direction. Additionally, the stiffening member includes strain relief slots distributed along the second side of the body and configured to expand so as to complement the compression slots in biasing the body to flex in the inward direction.

20 Claims, 9 Drawing Sheets

(51) Int. Cl.
*A61N 1/36* (2006.01)
*A61N 1/05* (2006.01)

(56) References Cited

U.S. PATENT DOCUMENTS

| | | | |
|---|---|---|---|
| 5,170,787 A | 12/1992 | Lindegren | |
| 5,722,425 A | 3/1998 | Bostrom | |
| 5,728,148 A | 3/1998 | Bostrom et al. | |
| 5,807,339 A | 9/1998 | Bostrom et al. | |
| 5,861,024 A | 1/1999 | Rashidi | |
| 6,156,027 A | 12/2000 | West | |
| 6,374,143 B1 * | 4/2002 | Berrang | A61N 1/0541 600/379 |
| 6,397,110 B1 | 5/2002 | Kuzma | |
| 8,112,161 B2 | 2/2012 | Jolly et al. | |
| 20,120,041 | 2/2012 | Dadd et al. | |
| 8,594,799 B2 | 11/2013 | Haller et al. | |
| 8,831,750 B2 | 9/2014 | Ramachandran et al. | |
| 8,886,331 B2 | 11/2014 | Labadie et al. | |
| 9,020,613 B2 | 4/2015 | Taylor et al. | |
| 9,033,869 B2 | 5/2015 | Thenuwara et al. | |
| 9,037,267 B2 | 5/2015 | Thenuwara et al. | |
| 9,211,403 B2 * | 12/2015 | Tortonese | A61M 25/0102 |
| 9,295,526 B2 | 3/2016 | Llinas et al. | |
| 9,492,654 B2 | 11/2016 | Thenuwara et al. | |
| 9,656,058 B2 | 5/2017 | Abbott et al. | |
| 2005/0234535 A1 * | 10/2005 | Risi | A61N 1/0541 607/57 |
| 2009/0030483 A1 | 1/2009 | Risi | |
| 2011/0066160 A1 * | 3/2011 | Simaan | A61N 1/05 606/129 |
| 2011/0251519 A1 | 10/2011 | Romoscanu | |
| 2011/0295352 A1 * | 12/2011 | Thenuwara | A61N 1/0541 607/137 |
| 2011/0301681 A1 | 12/2011 | Risi | |
| 2011/0319909 A1 | 12/2011 | Thenuwara et al. | |
| 2012/0035615 A1 | 2/2012 | Koester et al. | |
| 2012/0172893 A1 | 7/2012 | Taylor et al. | |
| 2013/0035551 A1 * | 2/2013 | Yu | A61B 1/0055 600/141 |
| 2013/0103112 A1 | 4/2013 | Risi et al. | |
| 2013/0296884 A1 | 11/2013 | Taylor et al. | |
| 2015/0025546 A1 | 1/2015 | Taylor et al. | |
| 2016/0096013 A1 | 4/2016 | Tortonese et al. | |
| 2018/0104473 A1 | 4/2018 | Purnell | |

FOREIGN PATENT DOCUMENTS

| | | |
|---|---|---|
| CN | 106573141 | 4/2017 |
| WO | 9840119 | 9/1998 |
| WO | 2004026199 | 4/2004 |
| WO | 2008058336 | 5/2008 |
| WO | 2010005627 | 1/2010 |

OTHER PUBLICATIONS

International Search Report and Written Opinion received in International Application No. PCT/US18/027626, dated Jun. 25, 2019.
Dosher, J. et al., Human Interaction with Small Haptic Effects, Presence, vol. 14, No. 3, Jun. 2005, 329-344.
Rebscher, S. et al., Considerations for the design of future cochlear implant electrode arrays: Electrode array stiffness, size and depth of insertion, J Rehabil Res Dev. 2008; 45(5): 731-748.

* cited by examiner

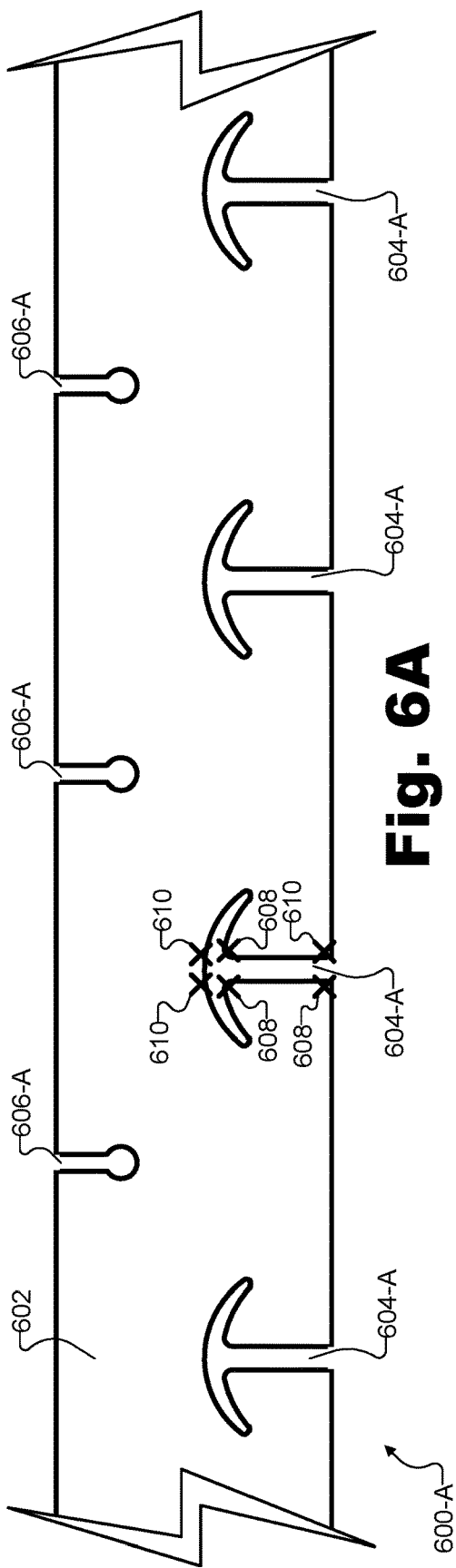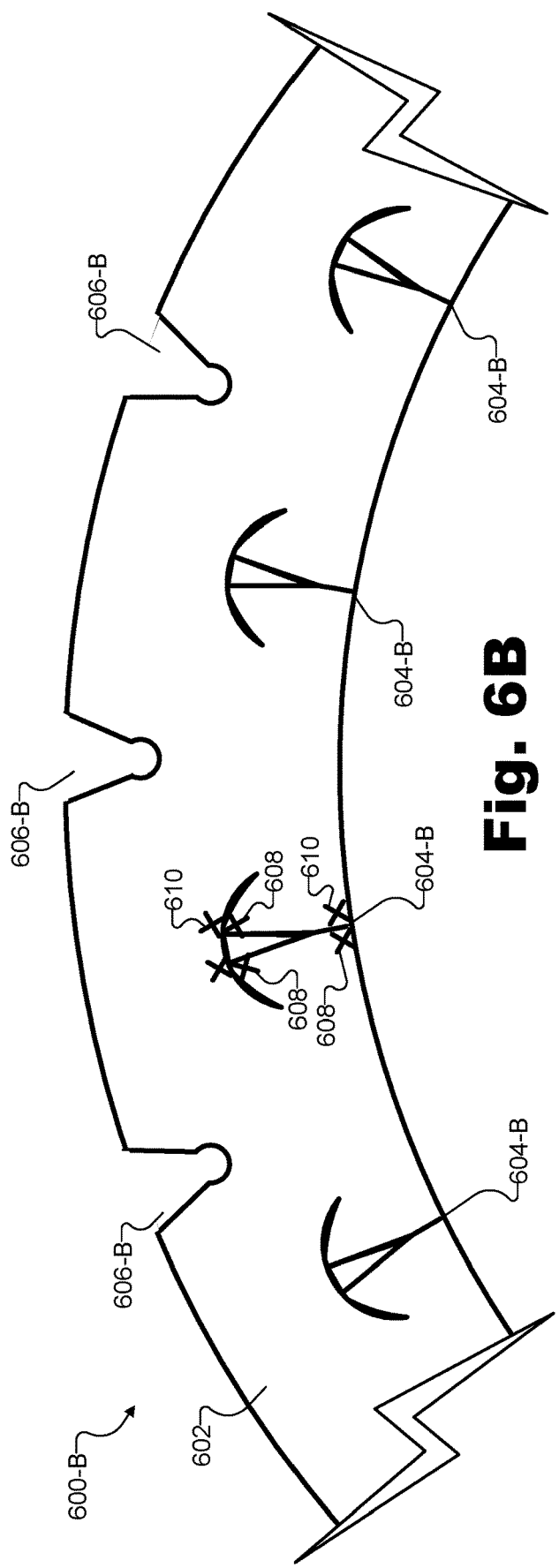

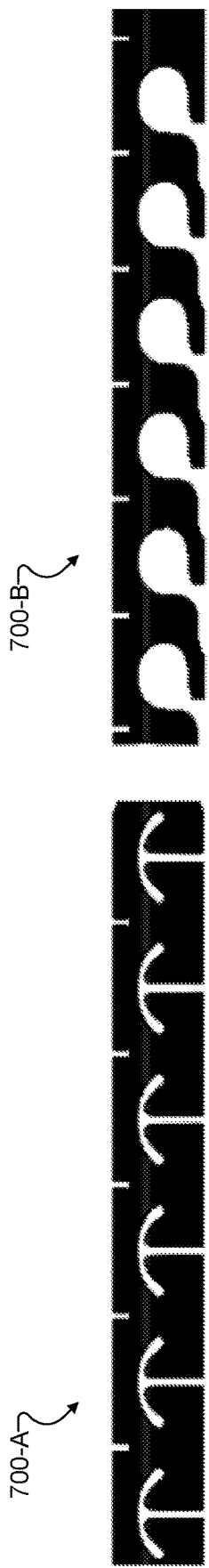
Fig. 7A
Fig. 7B
Fig. 7C
Fig. 7D

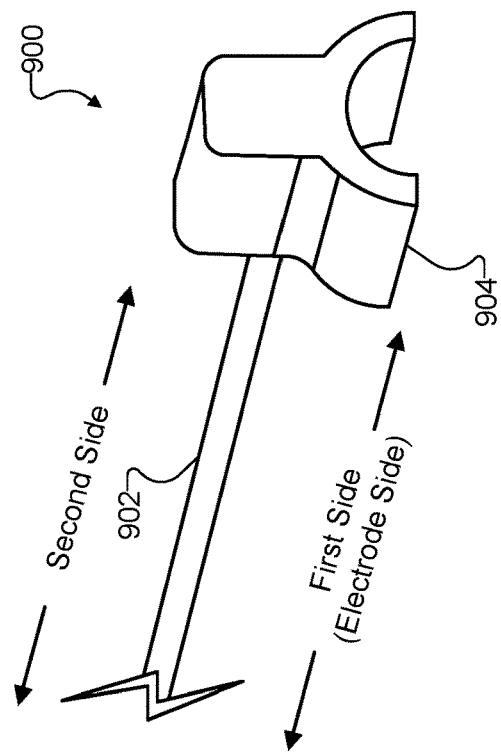
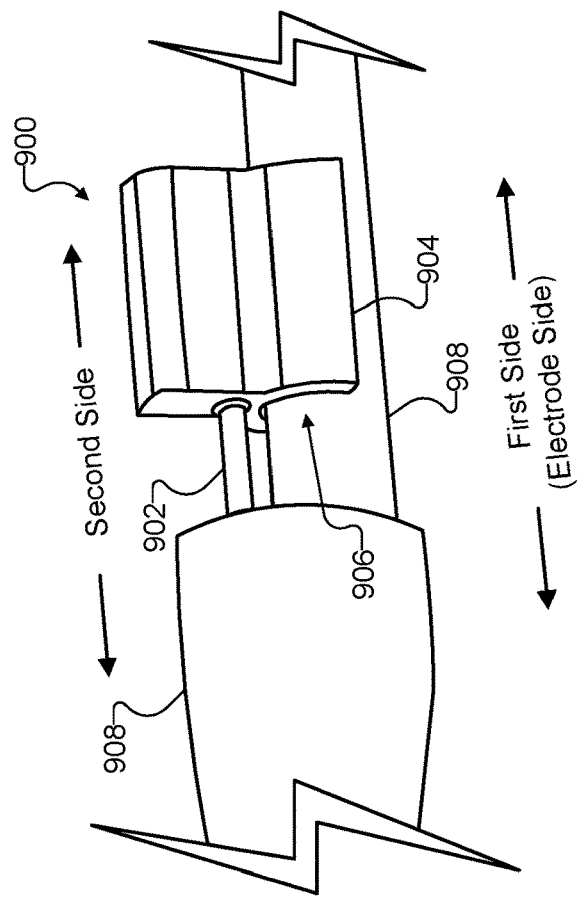

US 11,433,246 B2

SLOTTED STIFFENING MEMBER FOR FACILITATING AN INSERTION OF AN ELECTRODE LEAD INTO A COCHLEA OF A PATIENT

BACKGROUND INFORMATION

Cochlear implant systems are used to provide, restore, and/or improve hearing loss suffered by cochlear implant patients who use the cochlear implant systems. In operation, typical cochlear implant systems include one or more external components such as a microphone, a sound processor, and a headpiece that interoperate to control and direct one or more internal (e.g., implanted) components such as a cochlear implant and an electrode lead having a plurality of electrodes disposed along the electrode lead.

The electrode lead may be surgically implanted into the patient's cochlea to allow the plurality of electrodes disposed along the electrode lead to apply electrical stimulation generated by the cochlear implant to different areas of the cochlear tissue. Unfortunately, the surgical procedure by way of which an electrode lead is inserted into a patient's cochlea (referred to herein as an "insertion procedure") may be a delicate and difficult procedure to perform. Even when performed with great care and skill, an insertion procedure may result in trauma to the cochlea (e.g., which may lead to a reduction in residual hearing, pain or discomfort experienced by the patient, etc.), suboptimal electrode lead placement (e.g., which may lead to suboptimal cochlear implant system performance, etc.), and/or other undesirable results.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 6A illustrates a plurality of exemplary compression slots and a plurality of exemplary strain relief slots distributed along a body of an exemplary slotted stiffening member while the body is in a substantially linear configuration in an absence of a flexure force on the body according to principles described herein.

FIG. 6B illustrates the plurality of exemplary compression slots and the plurality of exemplary strain relief slots of FIG. 6A while the body of the slotted stiffening member is in a flexed configuration in a presence of the flexure force on the body according to principles described herein.

FIG. 7A illustrates an exemplary plurality of compression slots and strain relief slots that may be included on a slotted stiffening member such as the stiffening member of FIG. 3 according to principles described herein.

FIG. 7B illustrates another exemplary plurality of compression slots and strain relief slots that may be included on a slotted stiffening member such as the stiffening member of FIG. 3 according to principles described herein.

FIG. 7C illustrates yet another exemplary plurality of compression slots and strain relief slots that may be included on a slotted stiffening member such as the stiffening member of FIG. 3 according to principles described herein.

FIG. 7D illustrates yet another exemplary plurality of compression slots and strain relief slots that may be included on a slotted stiffening member such as the stiffening member of FIG. 3 according to principles described herein.

FIG. 9A illustrates an exemplary orientation retainer coupled to the body of an exemplary slotted stiffening member at a proximal end of the body according to principles described herein.

FIG. 9B illustrates the orientation retainer of FIG. 9A interfacing with an exemplary electrode lead to maintain a first side of the stiffening member to be closer to electrodes of the electrode lead than a second side opposite the first side according to principles described herein.

DETAILED DESCRIPTION

Figure 1:
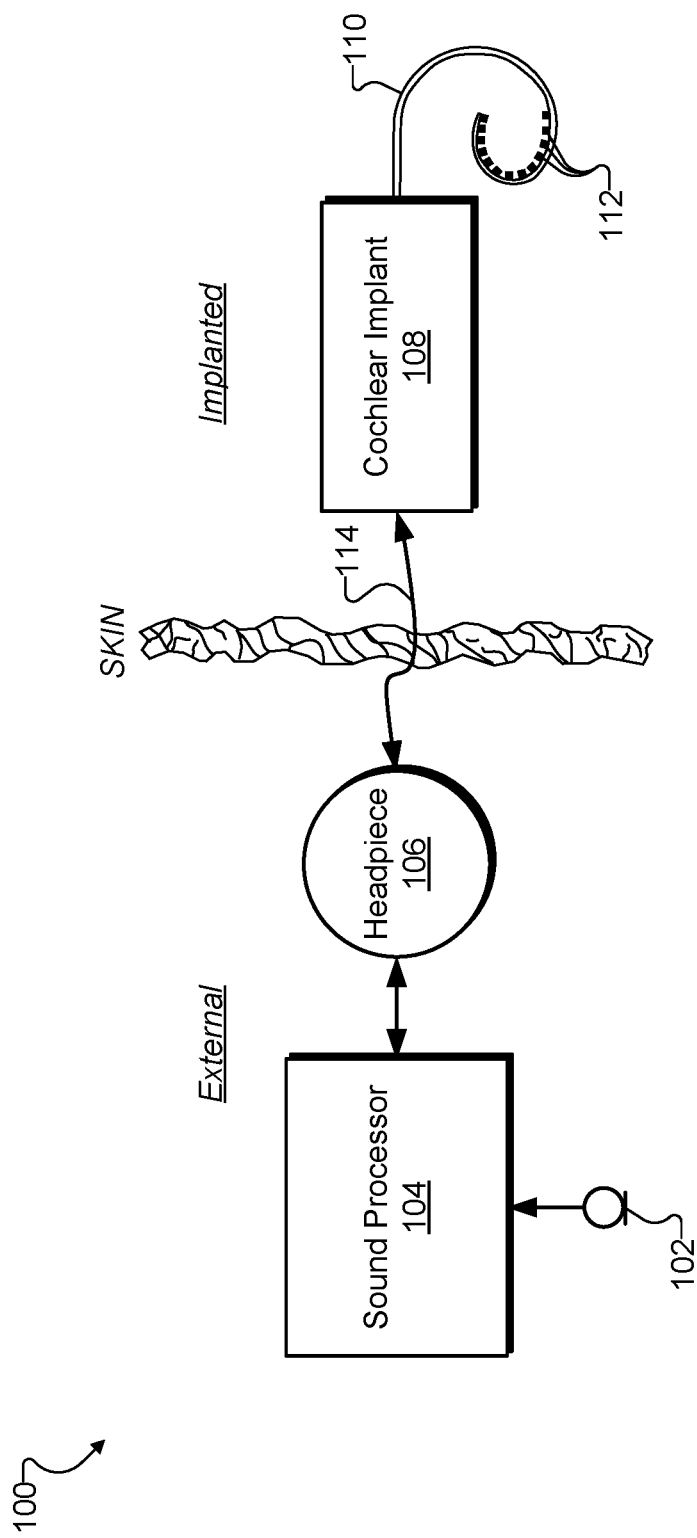
FIG. 1 illustrates an exemplary cochlear implant system according to principles described herein.

Implementations of a slotted stiffening member for facilitating an insertion of an electrode lead into a cochlea of a patient are described herein. For example, as will be described in more detail below, a stiffening member (e.g., a stylet, a stiffening sleeve, etc.) may be employed to facilitate an insertion, into a cochlea of a cochlear implant patient, of an electrode lead having a plurality of electrodes. Such a stiffening member may include an elongate body having a first side and a second side opposite the first side. The body of the stiffening member may be configured to integrate with a portion of the electrode lead along a length of the electrode lead so as to maintain the portion of the electrode lead in a substantially linear configuration in an absence of a flexure force on the body. For instance, while the body of the stiffening member is integrated with the electrode lead (e.g., by being encapsulated within a lumen of the electrode lead, by being overmolded over the portion of electrode lead, etc.), the first side of the body may be configured to be closer to the electrodes than the second side. The stiffening member may further include a plurality of compression slots distributed along the first side of the body and a plurality of strain relief slots distributed along the second side of the body. The plurality of compression slots may be configured to compress, in a presence of the flexure force, so as to bias the body of the stiffening member to flex in an inward direction. Similarly, the plurality of strain relief slots may be configured to expand in the presence of the flexure force so as to complement the plurality of compression slots in biasing the body to flex in the inward direction.

In some examples, as will be described in more detail below, a plurality of compression slots included on a slotted stiffening member may implement a predetermined stiffness profile. For instance, by being distributed along the first side of the body of the slotted stiffening member in a non-uniform distribution, the plurality of compression slots may make certain portions of the stiffening member relatively flexible (e.g., prone to flex in the presence of a flexure force) while making other portions of the stiffening member relatively stiff (e.g., not as prone to flex in the presence of the flexure force) in accordance with the predetermined stiffness profile. Similarly, a plurality of strain relief slots included on the slotted stiffening member may further implement the predetermined stiffness profile by being distributed along the second side of the body in a non-uniform distribution that corresponds to the non-uniform distribution of the plurality of compression slots. Along with being distributed in the non-uniform distribution along the body, the compression slots and/or strain relief slots may further implement the predetermined stiffness profile by including a difference in slot size among different compression slots or strain relief slots, a difference in slot type among different compression slots or strain relief slots, or in any other manner as may serve a particular implementation.

Various benefits may be provided by slotted stiffening members for facilitating insertion of electrode leads into cochleae of patients described herein. In particular, these slotted stiffening members may improve the outcome of electrode lead insertion procedures by making such procedures easier to perform consistently and successfully.

As mentioned above, electrode lead insertion procedures may typically be associated with a relatively large degree of risk of cochlear trauma due to the delicate nature of the cochlea and the difficulty of the insertion procedure. For instance, in examples where an electrode lead being inserted is overly stiff, the electrode lead may scrape the tissue of the cochlea rather than flexing when coming into contact with the tissue. In some cases, the electrode lead may even translocate from one cochlear chamber to another by penetrating a wall of the cochlear chamber into which the electrode lead is being inserted. Such trauma may result in a loss of residual hearing, pain and discomfort, and/or other negative consequences for the patient. Conversely, in examples where an electrode lead being inserted is overly flexible or limp, the electrode lead may be uncompliant and difficult to insert due to undesirable twisting, buckling, and so forth. In some examples, this resistance to comply with a surgeon's attempts to insert the electrode lead may similarly result in translocation or other cochlea trauma as excessive force may be applied to the electrode lead in an attempt to force the electrode lead to comply.

Fortunately, slotted stiffening members described herein may cause an electrode lead to have an optimized stiffness to flex when in contact with cochlear tissue (e.g., without causing trauma to the tissue) while not flexing so easily that the electrode lead becomes uncompliant and difficult to control (e.g., thus possibly requiring additional force to insert). Additionally, because the stiffness of a slotted stiffening member may be controlled by way of various factors such as slot distribution, slot size, slot type, and so forth as described above, slotted stiffening members may be customized and/or fine-tuned to implement any stiffness as may serve a particular implementation. In some examples, as mentioned above, slotted stiffening members may even be characterized by different stiffness gradients at different portions of the stiffening members in accordance with non-uniform predetermined stiffness profiles. For example, a slotted stiffening member may be made to be stiffer at portions where stiffness is desirable (e.g., near a distal tip of the electrode lead) and more flexible at portions where flexibility is desirable (e.g., near portions of the electrode lead configured to rest along certain curves of the cochlea). Moreover, because of the complementary placement of compression slots and strain relief slots on opposing sides of the slotted stiffening members, electrode leads may be biased (e.g., constrained, limited, etc.) to flex in only one direction (e.g., inwardly) or two directions (e.g., inwardly or outwardly), rather than to freely flex and twist in any direction including lateral directions that may be undesirable.

As a result of optimized and customized stiffness profiles made possible by slotted stiffening members described herein, as well as directional flexing and other benefits made possible by these slotted stiffening members, electrode lead insertion procedures involving slotted stiffening member described herein may be performed by hand with minimal or no additional tools. For instance, in certain examples, an insertion procedure may be performed by hand and without special tools by allowing the electrode lead to gently and unidirectionally flex as a result of flexure force from contact with the tissue of the cochlea. In other examples, an insertion procedure may be performed by hand using minimal tools such as a tool to facilitate control of a steering pull wire included within the stiffening member and configured to apply a flexure force on the stiffening member to thereby cause the stiffening member to flex while avoiding contact with the cochlear tissue.

Moreover, all of these benefits may be provided by slotted stiffening members that are relatively inexpensive and straightforward to manufacture. For example, rather than being made of costly noble metals such as platinum, slotted stiffening members described herein may be constructed from standard surgical stainless steel tubing or other suitable materials.

Additionally, the materials from which slotted stiffening members described herein may be constructed may retain their shape (e.g., without plastically deforming) when flexed as described herein. Accordingly, while such stiffening members may remain permanently integrated with the electrode lead after the insertion procedure in some examples, in other examples, it may be relatively straightforward to withdraw the stiffening members subsequent to the insertion procedure if that should be desirable. This may be advantageous in comparison to certain conventional stiffening members that plastically deform when flexed and thus would risk upsetting the configuration of an electrode lead within the cochlea if withdrawn subsequent to the insertion procedure.

Various embodiments will now be described in more detail with reference to the figures. The disclosed systems and methods may provide one or more of the benefits mentioned above and/or various additional and/or alternative benefits that will be made apparent herein.

In order to illustrate an exemplary context in which a slotted stiffening member for facilitating an insertion of an electrode lead into a cochlea of a patient may operate, FIG. 1 depicts an exemplary cochlear implant system 100. As shown, cochlear implant system 100 may include a microphone 102, a sound processor 104, a headpiece 106 having a coil disposed therein, a cochlear implant 108, and an electrode lead 110 including a plurality of electrodes 112. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the patient (e.g., also referred to herein as a user of cochlear implant system 100). Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may represent a sound processor having a processing component (e.g., including various computing components such as a processor, memory, communication interfaces, etc.), a battery component, and, in certain implementations, one or more other components such as an earhook component, a cable component (e.g., a cable communicatively coupling sound processor 104 with headpiece 106), and so forth. Sound processor 104 may be configured to process an audio signal (e.g., an acoustic audio signal detected by microphone 102, an electrical audio signal input by way of an auxiliary audio input port or a Clinician's Programming Interface ("CPI") device, etc.) and to direct stimulation representative of the audio signal to be presented to a user of cochlear implant system 100 (e.g., a cochlear implant patient). For example, the stimulation representative of the audio signal and directed by the sound processor component to be presented to the patient may be electrical stimulation generated by cochlear implant 108 and applied by electrodes 112 on electrode lead 110 implanted within the user.

Sound processor 104 may be configured to direct cochlear implant 108 to generate and apply electrical stimulation (also referred to herein as "stimulation current") representative of an audio signal to the patient. For example, sound processor 104 may direct cochlear implant 108 to apply electrode stimulation to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway.

Sound processor 104 may process the audio signal in accordance with a selected sound processing strategy or program to generate appropriate stimulation parameters for controlling cochlear implant 108. Sound processor 104 may be housed within any suitable housing. For example, sound processor 104 may be implemented as a behind-the-ear ("BTE") unit, a body worn unit, or the like.

In some examples, sound processor 104 may wirelessly transmit stimulation parameters (e.g., in the form of data words included in a forward telemetry sequence) and/or power to cochlear implant 108 by way of a wireless communication link 114 between headpiece 106 and cochlear implant 108 (e.g., a wireless link between a coil disposed within headpiece 106 and a coil included within or coupled to cochlear implant 108). To this end, headpiece 106 may be communicatively coupled to sound processor 104 and may include an antenna (e.g., a coil and/or one or more wireless communication components) configured to facilitate selective wireless coupling of sound processor 104 to cochlear implant 108. Additionally or alternatively, headpiece 106 may be used to selectively and wirelessly couple any other external device (e.g., a battery charger, etc.) to cochlear implant 108. Headpiece 106 may be configured to be affixed to the patient's head and positioned or aligned such that an antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transferred between sound processor 104 and cochlear implant 108 via wireless communication link 114 transcutaneously.

Cochlear implant 108 may include any type of implantable stimulator that may be used in association with systems described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. As shown, electrode lead 110 may be pre-curved so as to properly fit within the spiral shape of the cochlea. As such, electrodes 112 may all be disposed on one side of the electrode lead (e.g., the inward side in which electrode lead 110 is pre-curved, as shown). It will be understood that one or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 as it remains external to the cochlea while electrode lead 110 is disposed within the cochlea.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear locations) within the patient by way of electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
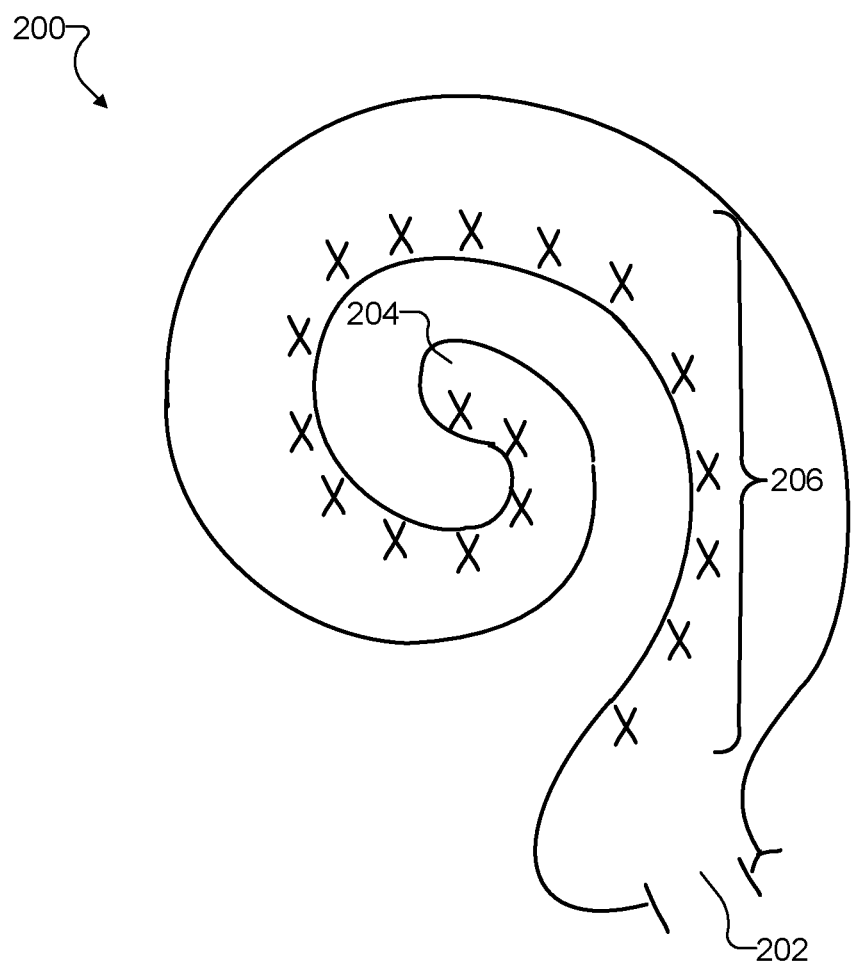
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206 (also referred to herein as cochlear tissue), which is denoted by Xs in FIG. 2. The auditory nerve tissue 206 is organized within the cochlea 200 in a tonotopic manner. Relatively low frequencies are encoded at or near apex 204 of cochlea 200 (referred to as an "apical region") while relatively high frequencies are encoded at or near base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

As mentioned above, a cochlear implant system such as cochlear implant system 100 may be used by a patient subsequent to an insertion procedure whereby an electrode lead such as electrode lead 110 is inserted into a cochlea of a patient such as cochlea 200. To facilitate such an insertion procedure, it may be desirable for the electrode lead to be stiff enough to be maneuvered into the cochlea without buckling, snagging, and/or encountering other issues described above. At the same time, it also may be desirable for the electrode lead to be flexible enough to easily flex when a significant flexure force is applied to the electrode lead (e.g., such as from making contact with cochlear tissue). For example, it would be desirable for the electrode lead to flex and give way to the cochlear tissue in the presence of such a force rather than to translocate through the tissue or otherwise cause trauma to the tissue. Moreover, it may further facilitate the insertion procedure if the electrode lead is able to flex in certain directions (e.g., in an inward direction such as illustrated in FIG. 1) without twisting or flexing in other directions (e.g., in lateral directions that do not conform to the shape of the cochlea, etc.).

To this end, an electrode lead assembly that includes a slotted stiffening member may be employed that meets these and other criteria for facilitating electrode lead insertion procedures. Specifically, an electrode lead assembly may include an electrode lead having an elongate lead body with a first side and a second side opposite the first side, a plurality of electrodes disposed along the first side of the lead body, and a stiffening member configured to facilitate an insertion of the electrode lead into a cochlea of a patient. The stiffening member may integrate with a portion of the electrode lead along a length of the electrode lead so as to maintain the portion of the electrode lead in a substantially linear configuration in an absence of a flexure force on the stiffening member. Additionally, the stiffening member may include a plurality of compression slots distributed along a first side of the stiffening member that corresponds to the first side of the lead body, and a plurality of strain relief slots distributed along a second side of the stiffening member that corresponds to the second side of the lead body. The plurality of compression slots may be configured to compress (e.g., in a presence of the flexure force) so as to bias the stiffening member to flex in an inward direction. Similarly, the plurality of strain relief slots may be configured to expand (e.g., in the presence of the flexure force) so as to complement the plurality of compression slots in biasing the stiffening member to flex in the inward direction.

Figure 3:
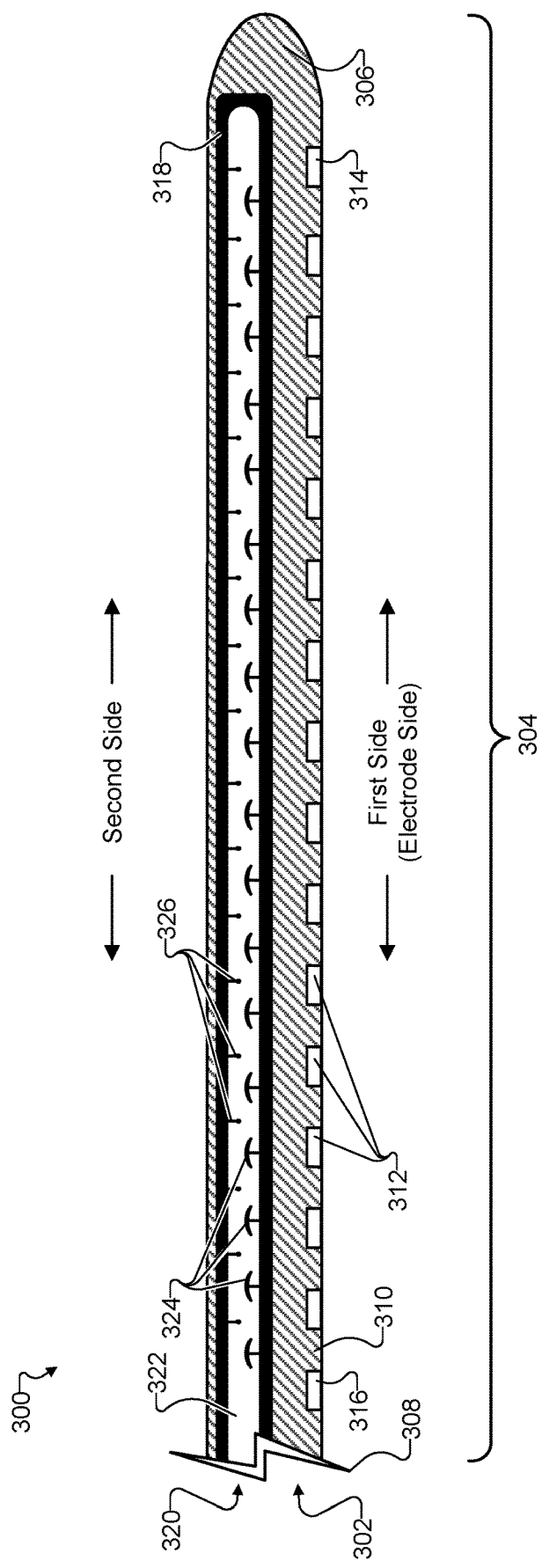
FIG. 3 illustrates an exemplary electrode lead assembly including an electrode lead and a slotted stiffening member for facilitating an insertion of the electrode lead into a cochlea of a patient according to principles described herein.

To illustrate, FIG. 3 depicts an exemplary electrode lead assembly 300 including an electrode lead and a slotted stiffening member for facilitating an insertion of the electrode lead into a cochlea of a patient. Specifically, FIG. 3 illustrates electrode lead assembly 300 in a substantially linear (e.g., straightened) configuration such as electrode lead assembly 300 may be in prior to an insertion procedure in which electrode lead assembly 300 is inserted into a cochlea of a patient. As shown, electrode lead assembly 300 includes an electrode lead 302, a distal portion 304 of which is depicted in FIG. 3. While distal portion 304 includes a distal tip 306 of electrode lead 302, it will be understood that a proximal portion 308 of electrode lead 302 is not explicitly illustrated in FIG. 3 but rather is represented by an omission symbol shown at a most proximal point on the portion of electrode lead 302 illustrated. It will be understood that proximal portion 308 of electrode lead 302 may extend past distal portion 304 to couple with a cochlear implant such as cochlear implant 108 beyond the omission symbol.

Electrode lead 302 may include an elongate lead body 310 having a first side and a second side opposite the first side, as labeled in FIG. 3. Along the first side of lead body 310, a plurality of electrodes 312 may be disposed, including a most distal electrode 314 and most proximal electrode 316. Because electrode lead 302 is configured to be inserted into a cochlea with distal end 306 entering first, electrodes 312 near proximal portion 308 may be referred to as basal electrodes, with electrode 316 being referred to as a most basal electrode. Similarly, electrodes near distal tip 306 may be referred to as apical electrodes, with electrode 314 being referred to as a most apical electrode. While additional electrodes (e.g., such as a ground electrode) may be included on proximal portion 308 (not shown), it will be understood that electrodes 312 disposed along the first side of lead body 310 may not be distributed along the entire length of the entire first side of lead body 310, but, rather, may be limited to distal portion 304, as shown. In a similar way, it will be understood that a slotted stiffening member may only integrate with a certain portion of electrode lead 302 (e.g., rather than integrating with an entire length of electrode lead 302), and/or that a slotted portion of the slotted stiffening member may correspond only to a certain portion of electrode lead 302 (e.g., distal portion 304) while other portions of the slotted stiffening member (e.g., portions corresponding to proximal portion 308 of electrode lead 302) may not include slots or other such features.

In the example of FIG. 3, electrode lead 302 is shown to further include a lumen 318 into which a stylet may be inserted. As such, a slotted stiffening member implemented as a stylet 320 may be encapsulated within lumen 318 to facilitate an insertion procedure of electrode lead assembly 300 into a cochlea of a patient. In certain examples, stylet 320 may be configured to be temporarily encapsulated in lumen 318 of electrode lead 302 so as to be removable from lumen 318 after a surgical insertion of electrode lead 302 into the cochlea of the patient. Conversely, in other examples, stylet 320 may be configured to be permanently encapsulated in lumen 318 of electrode lead 302 so as to remain encapsulated in lumen 318 after the surgical insertion of electrode lead 302 into the cochlea of the patient.

As shown in FIG. 3, stylet 320 may include an elongate body 322 having a first side and a second side opposite the first side and configured to be encapsulated within lumen 318 of electrode lead 302 so as to maintain electrode lead 302 in a substantially linear configuration in an absence of a flexure force on body 322. The first side of body 322 corresponds to the first side of the electrode lead and, as such, is configured to be closer to electrodes 312 than the second side of body 322 while body 322 is encapsulated within lumen 318 of electrode lead 302.

Body 322 may be constructed of any suitable material with any suitable plasticity limits. For instance, in some implementations, body 322 of stylet 320 may be constructed of a material that will plastically deform as body 322 flexes in the presence of a flexure force. In other words, even after the flexure force is removed, these implementations of stylet 320 may not return to the substantially linear configuration but may at least partially retain the flexed configuration. In other implementations, body 322 of stylet 320 may be constructed of a material that does not plastically deform (e.g., does not reach a limit of plasticity) as a result of an inward flexing of body 322 due to the presence of the flexure force, even when stylet 320 is inwardly flexed to a relatively large angle of deflection (e.g., up to 270°, up to 360°, etc.). In other words, even after such implementations of stylet 320 have been inwardly flexed significantly in the presence of a flexure force, body 322 may return to the substantially linear configuration illustrated in FIG. 3 upon removal of the flexure force causing the inward flexing. As mentioned above, such implementations may be advantageous if it is desirable for stylet 320 to be removed from lumen 318 after electrode lead assembly 300 has been inserted into the cochlea.

With these factors in mind, any of various suitable materials may be used to construct stylet 320. For example, a surgical grade stainless steel material (e.g., stainless steel surgical tubing, etc.) or a polymer material (e.g., polyimide tubing, PTFE tubing, etc.) may be used. Additionally, a coating may be applied to the material from which stylet 320 is constructed to reduce friction, protect the material, and so forth. For instance, a PARYLENE coating, PTFE coating, or other suitable coating may be employed.

As shown in FIG. 3, stylet 320 may include a plurality of compression slots 324 distributed along the first side of body 322, and a plurality of strain relief slots 326 distributed along the second side of body 322. The plurality of compression slots 324 may be configured to compress, in a presence of the flexure force, so as to bias the body to flex in an inward direction (e.g., to curl inward on the first side with the electrodes as illustrated by electrode lead 110 in FIG. 1). At the same time, the plurality of strain relief slots may be configured to expand, in the presence of the flexure force, so as to complement the plurality of compression slots in biasing the body to flex in the inward direction.

Slots 324 and 326 may be formed in any manner as may serve a particular implementation. For example, slots 324 and 326 may be formed in tubing material by way of a micromachining process, by laser cutting, or the like. In other examples, slots 324 and 326 may be formed by way of a molding process or in another suitable manner.

As shown, the plurality of compression slots 324 and the plurality of strain relief slots 326 are distributed along the first and second sides of the body, respectively, in respective uniform distributions that correspond to a uniform stiffness profile. Each plurality of slots includes slots that are all of an identical size and type, further contributing to a uniform stiffness throughout stylet 320. While such uniform slot distribution, size, and type may be advantageous in certain implementations, other implementations may include at least some variance in slot distribution, size, and/or type in order to implement a non-uniform stiffness profile. For example, the plurality of compression slots 324 included in stylet 320 may implement a predetermined stiffness profile by being distributed along the first side of body 322 in a non-uniform distribution in accordance with the predetermined stiffness profile, and the plurality of strain relief slots 326 may further implement the predetermined stiffness profile by being distributed along the second side of the body in a non-uniform distribution that corresponds to the non-uniform distribution of the plurality of compression slots 324.

Figure 4:
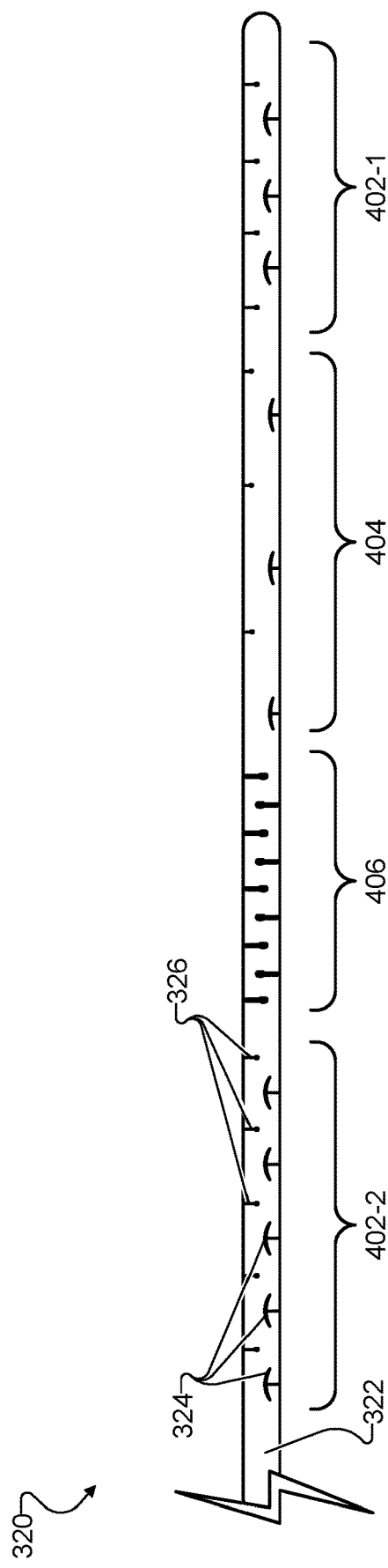
FIG. 4 illustrates an implementation of the slotted stiffening member of FIG. 3 that implements a predetermined stiffness profile according to principles described herein.

To illustrate, FIG. 4 shows an implementation of stylet 320 that implements a predetermined stiffness profile by including variance in slot distribution, size, and type. As shown, three different portions of body 322 of stylet 320, each characterized by different configurations of slots 324 and/or 326, are labeled in FIG. 4. Portion 402 (including two sub-portions 402-1 and 402-2) includes slots 324 and 326 that are similar in type, size, and spacing to the uniform stiffness profile illustrated in FIG. 3. However, different parts of the non-uniform stiffness profile are implemented by a portion 404 and a portion 406 of stylet 320.

As compared to portion 402, portion 404 includes a difference in slot size among different compression slots 324 in the plurality of compression slots 324 and a difference in slot size among different strain relief slots 326 in the plurality of strain relief slots 326 while generally keeping the respective slot types (e.g., the general shape of each slot) the same. Additionally, slots 324 and 326 in portion 404 are distributed with greater spacing in between slots as compared to the spacing in portion 402. As a result of either or both of these differences, portion 404 may be stiffer than portion 402.

In contrast, as compared to portion 402, portion 406 includes a difference in slot type among different compression slots 324 in the plurality of compression slots 324 as well as a difference in slot type among different strain relief slots 326 in the plurality of strain relief slots 326. Specifically, as will be described in more detail below, the compression slots 324 and strain relief slots 326 in portion 406 may be symmetrical so as to bias portion 406 to flex in either an inward direction or an outward direction while still limiting the ability of portion 406 to flex or twist in a lateral direction. Including a symmetrical portion such as portion 406 (i.e., a portion in which compression slots 324 and strain relief slots 326 are sized and shaped in the same way to facilitate bidirectional flexing) along with asymmetrical portions such as portions 402 and/or 404 (i.e., portions in which compression slots 324 and strain relief slots 326 are sized and shaped differently from one another to facilitate only unidirectional flexing) may be beneficial in certain implementations.

FIGS. 3 and 4 have illustrated and described different aspects of implementations of stylet 320 to illustrate one type of slotted stiffening member that may be used in an electrode lead assembly such as electrode lead assembly 300. However, stylets such as stylet 320 are only one example of how slotted stiffening members may be implemented to facilitate insertion of an electrode lead into a cochlea of a patient. In other implementations, slotted stiffening members may be implemented in ways other than stylets such as stylet 320. For example, a stiffening member may be implemented as a stiffening sleeve permanently overmolded along a portion of an electrode lead so as to remain integrated with the electrode lead after a surgical insertion of the electrode lead into a cochlea of a patient.

Figure 5:
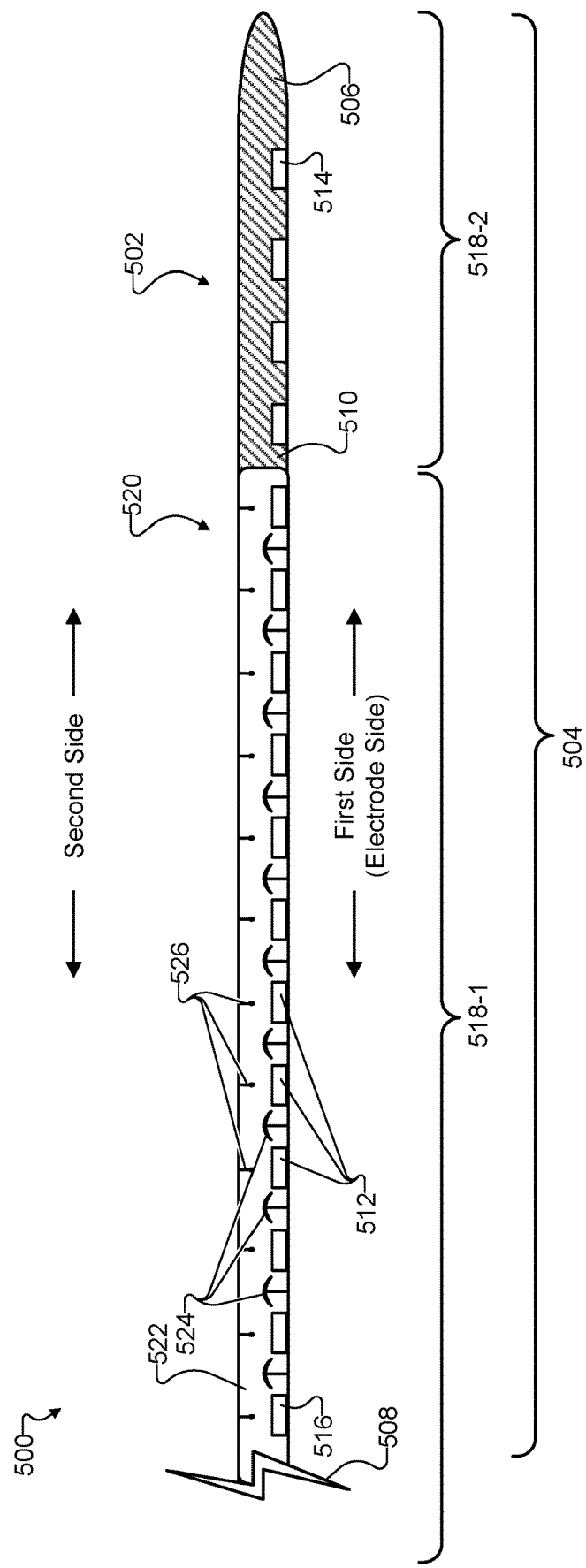
FIG. 5 illustrates an exemplary electrode lead assembly including an electrode lead and a slotted stiffening member implemented as a stiffening sleeve permanently overmolded along a portion of the electrode lead according to principles described herein.

To illustrate, FIG. 5 shows an exemplary electrode lead assembly 500 including an electrode lead and a slotted stiffening member implemented as a stiffening sleeve permanently overmolded along a portion of the electrode lead. FIG. 5 illustrates electrode lead assembly 500 in a substantially linear configuration such as electrode lead assembly 500 may be in prior to an insertion procedure in which electrode lead assembly 500 is inserted into a cochlea of a patient. Electrode lead assembly 500 includes various similar aspects and components as electrode lead assembly 300 described above and, as such, these aspects and components are numbered with corresponding reference numbers. Specifically, electrode lead assembly includes an electrode lead 502, a distal portion 504 of which is depicted in FIG. 5. Distal portion 504 of electrode lead 502 includes a distal tip 506, and, as with electrode lead assembly 300, it will be understood that a proximal portion 508 of electrode lead 502 is not explicitly illustrated but is represented by an omission symbol shown at a most proximal point on the portion of electrode lead 502 illustrated in FIG. 5.

Electrode lead 502 further includes an elongate lead body 510 having a first side and a second side opposite the first side, as labeled in FIG. 5. Along the first side of lead body 510, a plurality of electrodes 512 are shown to be disposed, including a most distal electrode 514 (e.g., a most apical electrode) and most proximal electrode 516 (e.g., a most basal electrode).

While electrode lead assembly 300 was shown in FIG. 3 to include a lumen 318 configured to encapsulate a stylet-type implementation of a slotted stiffening member, electrode lead assembly 500 does not include a corresponding lumen because electrode lead assembly 500 is supported by a different type of slotted stiffening member implementation. For example, electrode lead 502 may be a long lateral wall type electrode lead (e.g., an electrode lead that is longer than 27 millimeters and is configured to be inserted relatively deep into the patient's cochlea compared to certain other types of electrode leads). As such, electrode lead 502 may include two different portions 518 (e.g., a sleeved portion 518-1 and an unsleeved portion 518-2) differentiated by whether or not each is encapsulated by an implementation of a slotted stiffening member shown in FIG. 5 as a stiffening sleeve 520. As shown, stiffening sleeve 520 extends along sleeved portion 518-1 for part of distal portion 504 and the entire proximal portion 508 of electrode lead 502, while unsleeved portion 518-2 includes the most distal part of distal portion 504 (e.g., possibly including one or more of the most distal electrodes 512).

In certain examples, such as for long lateral wall type electrode leads configured to be inserted deeply into narrow and delicate apical portions of the cochlea, it may be desirable for a most distal portion of the electrode lead to be more flexible and soft than may be the case for shorter electrode leads that are not configured to be inserted so deeply into the cochlea. As such, unsleeved portion 518-2 may be very flexible as it is unsupported by any type of stiffening member. At the same time, such long electrode leads may need a relatively great amount of support at a more proximal portion (e.g., to support the relatively large weight and/or leveraged force that may be applied to the long electrode lead). As such, a relatively stiff stiffening sleeve 520 (or at least a stiffening sleeve 520 implementing a stiffness profile including certain regions that are relatively stiff) may be used to provide support along sleeved portion 518-1.

As shown in FIG. 5, stiffening sleeve 520 may include an elongate body 522 having a first side and a second side opposite the first side and configured to act as a stiffening sleeve for sleeved portion 518-1 (e.g., by being permanently overmolded along sleeved portion 518-1) so as to maintain electrode lead 502 in a substantially linear configuration in an absence of a flexure force on body 522. The first side of body 522 corresponds to the first side of electrode lead 502 and, as such, is configured to be closer to electrodes 512 than the second side of body 522 while body 522 is integrated with (e.g., permanently overmolded along) sleeved portion 518-1 of electrode lead 502.

As with body 322 of stylet 320 described above, body 522 of stiffening sleeve 520 may be constructed of any suitable material with any suitable plasticity limits. For instance, in some implementations, body 522 of stiffening sleeve 520 may be constructed of a material that will plastically deform as body 522 flexes in the presence of a flexure force. In other implementations, body 522 of stiffening sleeve 520 may be constructed of a material that does not plastically deform (e.g., does not reach a limit of plasticity) as a result of an inward flexing of body 522 due to the presence of the flexure force, even when stiffening sleeve 520 is inwardly flexed to a relatively large angle of deflection. As with stylet 320, any of various suitable materials may be used to construct stiffening sleeve 520, such as a surgical grade stainless steel material, a polymer material, or the like.

As shown in FIG. 5, stiffening sleeve 520 may include a plurality of compression slots 524 distributed along the first side of body 522, and a plurality of strain relief slots 526 distributed along the second side of body 522. The plurality of compression slots 524 may be configured to compress, in a presence of the flexure force, so as to bias body 522 to flex in an inward direction as described above with body 322 of stylet 320. At the same time, the plurality of strain relief slots 526 may be configured to expand, in the presence of the flexure force, so as to complement the plurality of compression slots 524 in biasing body 522 to flex in the inward direction. Slots 524 and 526 may be formed in any of the ways described herein or in any manner as may serve a particular implementation. Additionally, the plurality of compression slots 524 and the plurality of strain relief slots 526 may be distributed along the first and second sides of the body, respectively, in respective uniform or non-uniform distributions corresponding to any uniform or non-uniform stiffness profile as may serve a particular implementation. As described above in relation to the slots in stylet 320, slots 524 and 526 of stiffening sleeve 520 may also include slots that all have identical characteristics (e.g., slot size, slot type, etc.) or slots that have varying characteristics to implement a non-uniform stiffness profile.

Whether a slotted stiffening member is implemented as a stylet (e.g., such as stylet 320), as a stiffening sleeve (e.g., such as stiffening sleeve 520), or in some other suitable form, respective compression slots and strain relief slots distributed along the slotted stiffening member may function to guide, direct, allow, and/or otherwise bias a body of the slotted stiffening member to flex in a certain direction and with a certain degree of flexibility by compressing and/or expanding in the presence of a particular flexure force.

To illustrate, FIG. 6A shows a plurality of exemplary compression slots and a plurality of exemplary strain relief slots distributed along a body of an exemplary slotted stiffening member while the body is in a substantially linear configuration 600-A in an absence of a flexure force on the body, while FIG. 6B shows the same pluralities of compression slots and strain relief slots while the body is in a flexed configuration 600-B in a presence of the flexure force on the body. Specifically, in FIG. 6A, a portion of a body 602 of a slotted stiffening member (e.g., such as stylet 320 or stiffening sleeve 520 described above) is shown to include a plurality of unflexed (e.g., uncompressed) compression slots 604-A and a complementary plurality of unflexed (e.g., unexpanded) strain relief slots 606-A while no flexure force is applied to body 602. In FIG. 6B, the portion of body 602 is shown with a plurality of flexed (e.g., compressed)

compression slots 604-B and a complementary plurality of flexed (e.g., expanded) strain relief slots 606-B when the flexure force is applied to body 602.

Compression slots 604 (e.g., compression slots 604-A or 604-B depending on whether a flexure force is applied to body 602) and strain relief slots 606 (e.g., strain relief slots 606-A or 606-B depending on whether the flexure force is applied to body 602) may flex (e.g., compress or expand) in any manner and/or may take any form as may serve a particular implementation. For example, FIGS. 7A through 7D illustrate a few exemplary pluralities 700 (e.g., pluralities 700-A through 700-D, respectively) of compression slots and strain relief slots that may be included on a slotted stiffening member (e.g., such as stylet 320 or stiffening sleeve 520) in different implementations. As in FIG. 6A, in each plurality 700 of compression and strain relief slots in FIGS. 7A through 7D, compression slots are illustrated on the bottom while strain relief slots are illustrated on the top (e.g., such that an "inward" flexing would involve the ends of each respective slotted stiffening member portion flexing toward the bottom of the page).

In each example illustrated in FIGS. 7A through 7D, strain relief slots are shown to complement corresponding compression slots in a one-to-one manner where one strain relief slot is positioned above a midpoint between two adjacent compression slots. This may be an effective way for the strain relief slots to complement the biasing of the stiffening member body performed by the compression slots. However, it will be understood that this is not the only type of configuration by which strain relief slots may complement compression slots. For example, rather than a one-to-one relationship between compression slots and strain relief slots, there may be two or more compression slots for every one strain relief slot in certain examples, or only one compression slots for every two or more strain relief slots in other examples. As such, each strain relief slot may be disposed in any suitable location with respect to the one or more compression slots to which the strain relief slot corresponds (i.e., which the strain relief slot is configured to complement) as may serve a particular implementation.

In certain examples, as illustrated specifically in FIGS. 7A and 7B, compression slots may be different from their corresponding strain relief slots such as by being larger, differently shaped, more complex, or the like. For example, as illustrated by pluralities 700-A and 700-B, at least some of the compression slots in the pluralities are different in at least one of a slot size and a slot type from complementary strain relief slots in the pluralities. As used herein, such compression slots and strain relief slots may be referred to as "asymmetrical" to one another. Asymmetrical pluralities of compression and strain relief slots such as pluralities 700-A and 700-B may be advantageous in certain examples because they may bias a slotted stiffening member to flex only in an inward direction (e.g., while restricting the stiffening member from flexing in an outward direction opposite the inward direction and/or in any lateral direction).

In other examples, as illustrated specifically in FIGS. 7C and 7D, compression slots may be similar or identical to their corresponding strain relief slots (e.g., albeit in an inverse orientation) such as by sharing the same slot type, slot size, and/or other such characteristics. For example, as illustrated by pluralities 700-C and 700-D, at least some of the compression slots in the pluralities are equivalent in a slot size and a slot type with complementary strain relief slots in the pluralities. As used herein, such compression slots and strain relief slots may be referred to as "symmetrical" to one another. Symmetrical pluralities of compression and strain relief slots such as pluralities 700-C and 700-D may be advantageous in certain examples because they may bias a slotted stiffening member to flex either in an inward direction or in an outward direction opposite the inward direction (e.g., while still restricting the stiffening member from flexing in any lateral direction). In other words, due to the symmetry in compression slots and strain relief slots in these examples, each slot may act as a compression slot when the stiffening member flexes in one direction while acting as a strain relief slot when the stiffening member flexes in the opposite direction. Thus, when flexing in the outward direction (e.g., where both ends of each portion of the stiffening members flex toward the top of the page), the strain relief slots distributed along the top of the body may essentially switch into compression slots while the compression slots distributed along the bottom of the body may essentially switch into strain relief slots.

Either asymmetrical or symmetrical pluralities of compression and strain relief slots may, in certain examples, include spring-back features to help control flexibility of the stiffening member body during different phases of flexing motion. For example, at least some of the compression slots in a plurality of compression slots may be spring-back cuts configured to mechanically provide a first degree of stiffness during an initial phase of a flexing motion and a second degree of stiffness during a subsequent phase of the flexing motion, where the second degree of stiffness is greater than the first degree of stiffness.

Returning to FIGS. 6A and 6B, configurations 600-A and 600-B illustrate how exemplary spring-back features may operate with "mushroom-shaped" spring-back compression slots such as compression slots 604. It will be understood that the spring-back principles described in relation to compression slots 604 may similarly apply to any of the compression slots in the pluralities of slots 700 in FIGS. 7A through 7D. As shown on one of the compression slots 604 in FIG. 6A, various contact points 608 do not contact corresponding contact points 610, allowing the compression slot 604 to compress with a relatively low degree of stiffness (i.e., a relatively high degree of flexibility) during an initial phase of a flexing motion (e.g., when body 602 is initially flexed out of substantially linear configuration 600-A toward flexed configuration 600-B). However, as shown on the same compression slot 604 in FIG. 6B, contact points 608 may each make physical contact with corresponding contact points 610 in flexed configuration 600-B, thus forcing compression slot 604 to have a higher degree of stiffness (i.e., a lower degree of flexibility) if it is to compress further during a subsequent phase of a flexing motion (e.g., when body 602 has already flexed to a desirable angle of deflection).

A flexure force causing substantially linear configuration 600-A to flex into flexed configuration 600-B may originate from any of various sources. For example, a flexure force on a body of a slotted stiffening member may be present as a result of contact between tissue of a cochlea of a patient and the slotted stiffening member or another part of an electrode lead assembly of which the slotted stiffening member is a part. For example, the flexure force may originate from contact between cochlear tissue and a portion of the electrode lead integrated with the body of the stiffening member. As another example, a flexure force on the body of a slotted stiffening member may be present as a result of tension applied to a pull wire coupled with (e.g. welded to) a distal tip of the stiffening member, or as a result of another suitable force applied in another way as may serve a particular implementation.

However, it will be understood that forces of gravity (e.g., gravity on the stiffening member due to its own weight), fluid pressure (e.g., air pressure or cochlear fluid pressure during an insertion procedure or the like), and/or other forces that may be present for a stiffening member during an insertion procedure prior to when it becomes desirable for the stiffening member to begin to flex (e.g., when a distal tip of the electrode lead encounters a first turn within the cochlea), may not be sufficient forces to be considered "flexure forces" as that term is used herein. In other words, a slotted stiffening member may be stiff enough to maintain substantially linear configuration 600-A when these various minor forces are present, but may flex in the presence of a flexure force such as from tissue contact, pull wire tension, or the like.

Figure 8A:
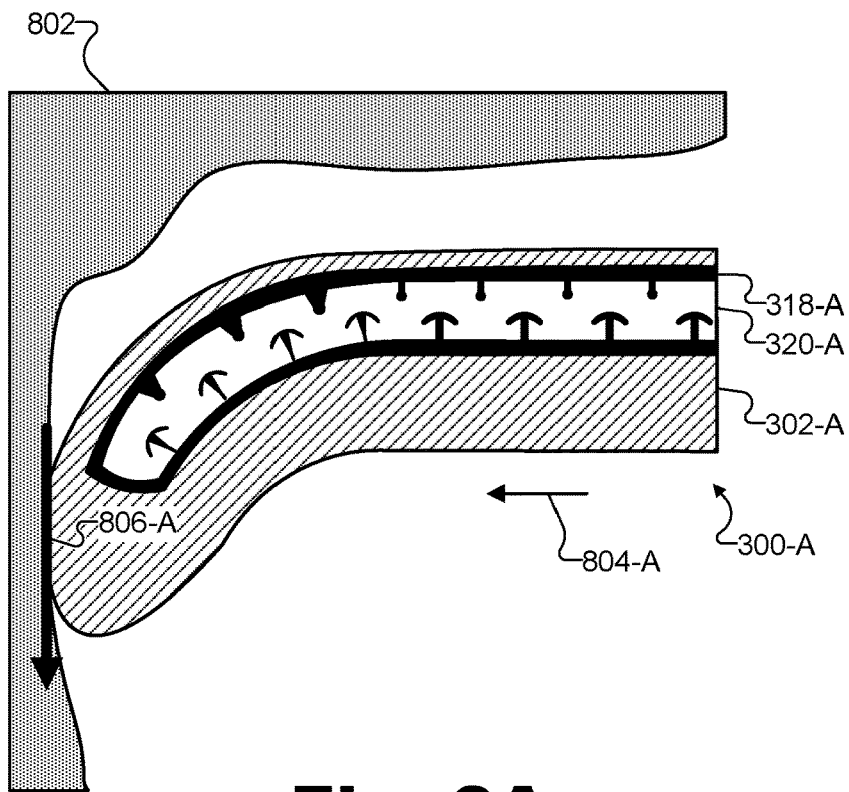
FIG. 8A illustrates an implementation of the electrode lead assembly of FIG. 3 flexing under a flexure force present as a result of contact between tissue of a cochlea of a patient and an electrode lead integrated with the stiffening member according to principles described herein.

To illustrate, FIG. 8A depicts an implementation 300-A of electrode lead assembly 300 (i.e., the electrode lead assembly of FIG. 3 including the slotted stiffening member implemented as stylet 320) flexing under a flexure force present as a result of contact between tissue of a cochlea of a patient and an electrode lead integrated with the stiffening member during an exemplary insertion procedure. Specifically, as shown, the implementation 300-A of electrode lead assembly 300 ("electrode lead assembly 300-A") includes an electrode lead 302-A having a lumen 318-A in which a stylet 320-A is encapsulated. It will be understood that various aspects of electrode lead assembly 300 and/or components thereof that are not specifically shown or labeled in FIG. 8A for clarity may be present and may function as described above in relation to electrode lead assembly 300.

Electrode lead assembly 300-A is being inserted into a cochlea 802 by way of an insertion procedure 804-A. At a moment during insertion procedure 804-A depicted in FIG. 8A, electrode lead assembly 300-A (e.g., electrode lead 302-A in particular) has made physical contact with tissue of cochlea 802, thus exerting a flexure force 806-A on electrode-lead 302-A. In turn, flexure force 806-A is also shown to be responsible for flexing stylet 320-A within lumen 318-A. As such, some of the compression slots on stylet 320-A have compressed and some of the strain relief slots have expanded to bias the body of stylet 320-A to flex in the inward direction with an optimized degree of flexibility that does not cause trauma to the tissue of cochlea 802. Because stylet 320-A guides and controls the flexing of electrode lead assembly 300-A in this way, insertion procedure 804-A may be performed by a surgeon (e.g., by hand without robotic or computerized assistance) without special tools or equipment sometimes used to facilitate insertion procedures. As the surgeon gently inserts electrode lead assembly 300-A into cochlea 802, stylet 320-A may gently direct the flexure of electrode lead assembly 300-A to conform to the curvature of cochlea 802 without causing cochlear trauma such as a translocation.

Figure 8B:
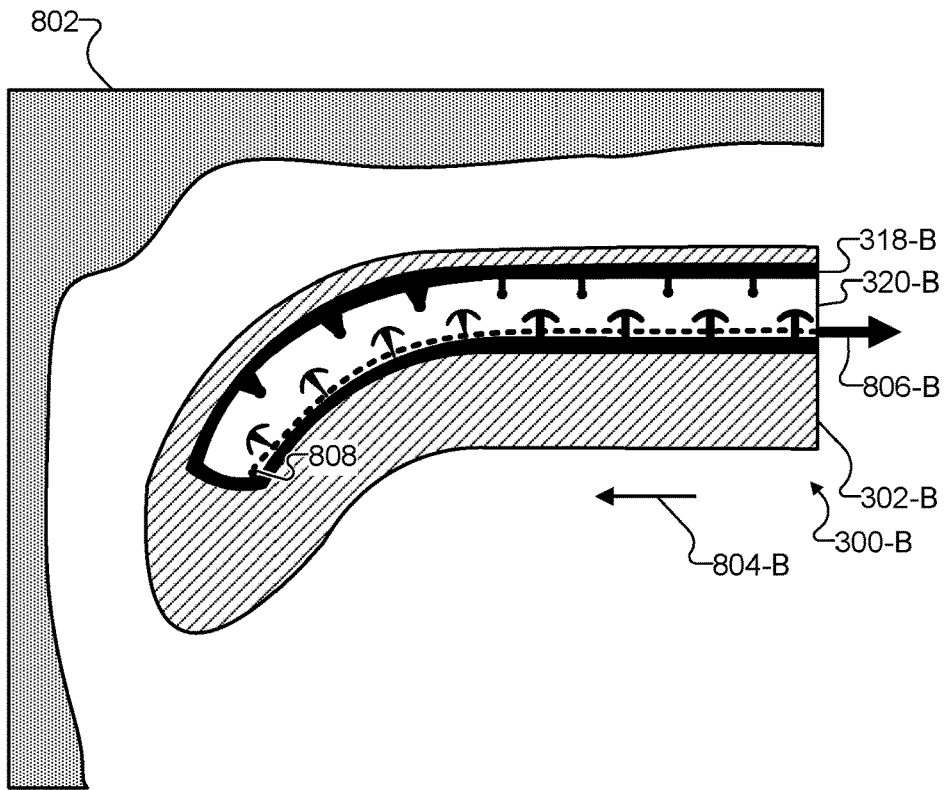
FIG. 8B illustrates an implementation of the electrode lead assembly of FIG. 3 flexing under a flexure force present as a result of tension applied to a pull wire coupled with a distal tip of the stiffening member according to principles described herein.

As another example, FIG. 8B depicts a similar but different implementation 300-B of electrode lead assembly 300 flexing under a flexure force present as a result of tension applied to a pull wire coupled with a distal tip of the stiffening member during an exemplary insertion procedure. Specifically, as shown, the implementation 300-B of electrode lead assembly 300 ("electrode lead assembly 300-B") includes an electrode lead 302-B having a lumen 318-B in which a steerable stylet 320-B is encapsulated. As with FIG. 8A above, it will be understood that various aspects of electrode lead assembly 300 and/or components thereof that are not specifically shown or labeled in FIG. 8B for clarity may still be present and may function as described above.

Electrode lead assembly 300-B is being inserted into cochlea 802 by way of an insertion procedure 804-B. At a moment during insertion procedure 804-B depicted in FIG. 8B, electrode lead assembly 300-B has begun to flex even though it has not made physical contact with tissue of cochlea 802. Instead, a flexure force 806-B is illustrated as a tension on a pull wire 808 coupled (e.g., welded, etc.) to a distal tip of stylet 320-B. As shown, when the tension is applied to pull wire 808 (e.g., by a surgeon performing insertion procedure 804-B using a tool that facilitates applying tension to pull wire 808), some of the compression slots on stylet 320-B have compressed, some of the strain relief slots have expanded, and the body of stylet 320-B has flexed in accordance with the inward flex biasing implemented by the slots. Because pull wire 808 may guide and control stylet 320-B to flex electrode lead assembly 300-B in this way, insertion procedure 804-B may be performed by a surgeon (e.g., by hand without robotic or computerized assistance) using minimal tools (e.g., a tool configured to facilitate applying tension to pull wire 808). As the surgeon inserts electrode lead assembly 300-B into cochlea 802, stylet 320-B may be steered using pull wire 808 to flex electrode lead assembly 300-B to conform to the curvature of cochlea 802 without causing cochlear trauma such as a translocation. Indeed, in certain examples, the surgeon may steer electrode lead assembly 300-B into cochlea 802 with little or no contact at all between electrode lead assembly 300-B and the tissue of cochlea 802. Active steering of electrode lead assembly 300-B into cochlea 802 by way of insertion procedure 804-B may be based on pre-planning or any suitable type of intraoperative monitoring or feedback. In some examples, a surgeon may perform insertion procedure 804-B, including actively steering stylet 320-B, using only one hand.

As insertion procedures such as insertion procedures 804-A or 804-B are performed using stylets encapsulated within respective lumens of electrode lead assemblies to control the flexing of the electrode lead assemblies, it is important for the stylets to remain properly oriented within the lumens. For example, if a stylet were to twist or rotate so that the first side of the stylet (i.e., the side on which the compression slots are disposed) is no longer facing the first side of the electrode lead (i.e., the side on which the electrodes are disposed), the electrode lead assembly may flex in undesirable directions and/or the insertion procedure may otherwise be compromised. Accordingly, it may be desirable to ensure that a unidirectional or bidirectional manner in which a stylet is biased to flex remain aligned with how a surgeon desires an electrode lead encapsulating the stylet to flex.

To this end, a stiffening member such as a stylet (or a stiffening sleeve that is not permanently overmolded along an electrode lead) may by constructed to include an orientation retainer coupled to the body of the stiffening member at a proximal end of the body. As such, the first side of the body may be configured to remain closer to the electrodes than the second side (i.e., remain properly aligned as described above) while the body is integrated with the electrode lead due to an interfacing of the orientation retainer with the electrode lead.

To illustrate, FIG. 9A depicts an exemplary orientation retainer coupled to the body of an exemplary slotted stiffening member at a proximal end of the body. Specifically, FIG. 9A illustrates a proximal end of an exemplary stylet 900 that includes a body 902 and is coupled to an orientation retainer 904, implemented as a mechanical feature configured to interface with a body of an electrode lead. While compression slots and strain relief slots are not illustrated on body 902 of stylet 900, it will be understood that such slots may be disposed on the first and seconds sides, respectively, on a distal portion of stylet 900 not explicitly shown (e.g., as illustrated in relation to other stylets above).

FIG. 9B illustrates orientation retainer 904 interfacing with an exemplary electrode lead to maintain a first side of body 902 of stylet 900 to be closer to electrodes of the electrode lead than a second side opposite the first side. Specifically, orientation retainer 904 is seated, connected, mated, attached, or otherwise interfaced at an interface location 906 with a body of an electrode lead 908. While orientation retainer 904 is illustrated to be able to slide along the body of electrode lead 908 to some degree, it will be understood that other features of electrode lead 908 may, in some implementations, hold orientation retainer 904 in place so that interface location 906 remains at a static position on the lead body. Additionally, while one type of orientation retainer and lead body are illustrated in FIGS. 9A and 9B, it will be understood that various other suitable designs for retaining the orientation of the first and second sides of body 902 of stylet 900 with respect to electrode lead 908 may be employed as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A stiffening member for facilitating an insertion of an electrode lead having a plurality of electrodes into a cochlea of a patient, the stiffening member comprising:
    an elongate body having a first side and a second side opposite the first side and configured to integrate with a portion of the electrode lead along a length of the electrode lead so as to maintain the portion of the electrode lead in a substantially linear configuration in an absence of a flexure force on the body, the first side configured to be closer to the electrodes than the second side while the body is integrated with the electrode lead;
    a plurality of compression slots of a first slot type distributed along the first side of the body, the plurality of compression slots configured to compress, in a presence of the flexure force, so as to bias the body to flex in an inward direction;
    a plurality of strain relief slots of a second slot type distributed along the second side of the body, wherein the second slot type is differently shaped from the first slot type and the plurality of strain relief slots is configured to expand, in the presence of the flexure force, so as to complement the plurality of compression slots in biasing the body to flex in the inward direction; and
    an orientation retainer coupled to the body at a proximal end of the body and configured to interface with the electrode lead to maintain, while the body is integrated with the electrode lead, the first side of the body closer to the electrodes than the second side of the body.

2. The stiffening member of claim 1, wherein:
    the plurality of compression slots implements a predetermined stiffness profile by being distributed along the first side of the body in a non-uniform distribution in accordance with the predetermined stiffness profile; and
    the plurality of strain relief slots further implements the predetermined stiffness profile by being distributed along the second side of the body in a non-uniform distribution that corresponds to the non-uniform distribution of the plurality of compression slots.

3. The stiffening member of claim 2, wherein at least one of the plurality of compression slots and the plurality of strain relief slots further implements the predetermined stiffness profile by including at least one of:
    a difference in slot size among different compression slots in the plurality of compression slots; or
    a difference in slot size among different strain relief slots in the plurality of strain relief slots.

4. The stiffening member of claim 2, wherein:
    the plurality of compression slots are distributed along the first side of the body with non-uniform spacing; and
    the plurality of strain relief slots are distributed along the second side of the body with non-uniform spacing.

5. The stiffening member of claim 1, wherein the plurality of compression slots and the plurality of strain relief slots are distributed along the first and second sides of the body, respectively, in respective uniform distributions that correspond to a uniform stiffness profile.

6. The stiffening member of claim 1, wherein at least some of the compression slots in the plurality of compression slots are different in slot size from complementary strain relief slots in the plurality of strain relief slots such that body is biased to flex only in the inward direction.

7. The stiffening member of claim 1, further comprising one or more additional compression slots distributed along the first side of a portion of the body and one or more additional strain relief slots distributed along the second side of the portion of the body and complementary to the one or more additional compression slots,
    wherein the one or more compression slots are equivalent in a slot size and a slot type with the one or more additional strain relief slots complementary to the one or more additional compression slots such that the portion of the body is biased to flex either in the inward direction or in an outward direction opposite the inward direction.

8. The stiffening member of claim 1, wherein:
    of the compression slots of the first slot type are spring-back cuts configured to mechanically provide a first degree of stiffness during an initial phase of a flexing motion and a second degree of stiffness during a subsequent phase of the flexing motion; and
    the second degree of stiffness is greater than the first degree of stiffness.

9. The stiffening member of claim 1, wherein:
    the body of the stiffening member is constructed of a material that does not plastically deform as a result of an inward flexing of the body due to the presence of the flexure force; and
    the body is configured to return, after the inward flexing, to the substantially linear configuration upon removal of the flexure force causing the inward flexing.

10. The stiffening member of claim 1, wherein the flexure force on the body is present as a result of contact between tissue of the cochlea of the patient and the portion of the electrode lead integrated with the body of the stiffening member.

11. The stiffening member of claim 1, wherein the flexure force on the body is present as a result of tension applied to a pull wire coupled with a distal tip of the stiffening member.

12. The stiffening member of claim 1, wherein the stiffening member is implemented as a stylet configured to be temporarily encapsulated in a lumen of the electrode lead so as to be removable from the lumen after a surgical insertion of the electrode lead into the cochlea of the patient.

13. The stiffening member of claim 1, wherein the stiffening member is implemented as a stylet configured to be permanently encapsulated in a lumen of the electrode lead so as to remain encapsulated in the lumen after a surgical insertion of the electrode lead into the cochlea of the patient.

14. An electrode lead assembly comprising:
an electrode lead including:
an elongate lead body having a first side and a second side opposite the first side, and
a plurality of electrodes disposed along the first side of the lead body; and
a stiffening member configured to facilitate an insertion of the electrode lead into a cochlea of a patient by integrating with a portion of the electrode lead along a length of the electrode lead so as to maintain the portion of the electrode lead in a substantially linear configuration in an absence of a flexure force on the stiffening member, the stiffening member including:
a plurality of compression slots of a first slot type distributed along a first side of the stiffening member that corresponds to the first side of the lead body, the plurality of compression slots configured to compress, in a presence of the flexure force, so as to bias the stiffening member to flex in an inward direction,
a plurality of strain relief slots of a second slot type distributed along a second side of the stiffening member that corresponds to the second side of the lead body, wherein the second slot type is differently shaped from the first slot type and the plurality of strain relief slots is configured to expand, in the presence of the flexure force, so as to complement the plurality of compression slots in biasing the stiffening member to flex in the inward direction, and
an orientation retainer at a proximal end of the stiffening member, the orientation retainer configured to interface with the electrode lead to maintain, while the stiffening member is integrated with the portion of the electrode lead, the first side of the stiffening member closer to the electrodes than the second side of the stiffening member.

15. The electrode lead assembly of claim 14, wherein:
the plurality of compression slots implements a predetermined stiffness profile by being distributed along the first side of the stiffening member in a non-uniform distribution in accordance with the predetermined stiffness profile; and
the plurality of strain relief slots further implements the predetermined stiffness profile by being distributed along the second side of the stiffening member in a non-uniform distribution that corresponds to the non-uniform distribution of the plurality of compression slots.

16. The electrode lead assembly of claim 15, wherein at least one of the plurality of compression slots and the plurality of strain relief slots further implements the predetermined stiffness profile by including at least one of:
a difference in slot size among different compression slots in the plurality of compression slots; or
a difference in slot size among different strain relief slots in the plurality of strain relief slots.

17. The electrode lead assembly of claim 15, wherein:
the plurality of compression slots of the stiffening member are distributed along the first side of the stiffening member with non-uniform spacing; and
the plurality of strain relief slots of the stiffening member are distributed along the second side of the stiffening member with non-uniform spacing.

18. A stylet for facilitating an insertion of an electrode lead having a plurality of electrodes into a cochlea of a patient, the stylet comprising:
an elongate body having a first side and a second side opposite the first side and configured to be encapsulated within a lumen of the electrode lead so as to maintain the electrode lead in a substantially linear configuration in an absence of a flexure force on the body, the first side configured to be closer to the electrodes than the second side while the body is encapsulated within the lumen of the electrode lead;
a plurality of compression slots of a first slot type distributed along the first side of the body, the plurality of compression slots configured to compress, in a presence of the flexure force, so as to bias the body to flex in an inward direction;
a plurality of strain relief slots of a second slot type distributed along the second side of the body, wherein the second slot type is differently shaped from the first slot type and the plurality of strain relief slots is configured to expand, in the presence of the flexure force, so as to complement the plurality of compression slots in biasing the body to flex in the inward direction; and
an orientation retainer coupled to the body at a proximal end of the body and configured to interface with the electrode lead to maintain, while the body is integrated with the electrode lead, the first side of the body closer to the electrodes than the second side of the body;
wherein the body of the stylet is constructed of a material that does not plastically deform as a result of an inward flexing of the body due to the presence of the flexure force, such that the body is configured to return, after the inward flexing, to the substantially linear configuration upon removal of the flexure force causing the inward flexing.

19. The stylet of claim 18, wherein:
the plurality of compression slots implements a predetermined stiffness profile by being distributed along the first side of the body in a non-uniform distribution in accordance with the predetermined stiffness profile; and
the plurality of strain relief slots further implements the predetermined stiffness profile by being distributed along the second side of the body in a non-uniform distribution that corresponds to the non-uniform distribution of the plurality of compression slots.

20. The stylet of claim 19, wherein at least one of the plurality of compression slots and the plurality of strain relief slots further implements the predetermined stiffness profile by including at least one of:
a difference in slot size among different compression slots in the plurality of compression slots; or a difference in slot size among different strain relief slots in the plurality of strain relief slots.

* * * * *